United States Patent [19]

Selleri

[11] Patent Number: 5,361,027
[45] Date of Patent: Nov. 1, 1994

[54] APPARATUS FOR NON-CONTACT DYNAMIC INSPECTIONS OF A PLURALITY OF PIECES

[75] Inventor: Narciso Selleri, Monteveglio, Italy

[73] Assignee: Marposs Societa' Per Azioni, S. Marino di Bentivoglio, Italy

[21] Appl. No.: 974,594

[22] PCT Filed: Aug. 29, 1991

[86] PCT No.: PCT/EP91/01637
 § 371 Date: Mar. 1, 1993
 § 102(e) Date: Mar. 1, 1993

[87] PCT Pub. No.: WO92/05398
 PCT Pub. Date: Apr. 2, 1992

[30] Foreign Application Priority Data

Sep. 14, 1990 [IT] Italy .................. 3651 A/90

[51] Int. Cl.⁵ ............... G01N 27/90; B65G 47/26; B07C 5/00
[52] U.S. Cl. ................... 324/226; 33/549; 198/339.1; 209/539; 324/261; 324/262
[58] Field of Search .............. 324/226, 238–243, 324/261, 262; 33/549; 198/339.1, 340, 418, 502.1, 502.2; 209/539, 546, 917, 918

[56] References Cited

U.S. PATENT DOCUMENTS 3,539,006 11/1970 Hanna et al. .............. 324/238 X
3,706,027 12/1972 Grice, Jr. et al. .............. 324/226
3,863,352 2/1975 Peonski .
3,975,829 8/1976 Possati .
4,507,610 3/1985 Nakaoka .
4,864,239 9/1989 Casarcia et al. .

FOREIGN PATENT DOCUMENTS 7791487 3/1988 Australia .
1100302 2/1961 Germany .
3228382 2/1983 Germany .

Primary Examiner—Gerard R. Strecker
Attorney, Agent, or Firm—Stevens, Davis, Miller & Mosher

[57] ABSTRACT

An apparatus for checking the surface condition of rollers for bearings, in particular barrel rollers, in which the pieces are conveyed and lined up in a row towards a checking station. In order to ensure the correct positioning of each piece during the checking operations, a compression force is applied to a section of the row, and in particular a thrust and a resisting action are applied at the ends of the section, urging the pieces of the section against one another in the course of their translation along a feed direction. Checking operations, for example through eddy current rotating heads, are carried out on pieces of the section.

6 Claims, 1 Drawing Sheet

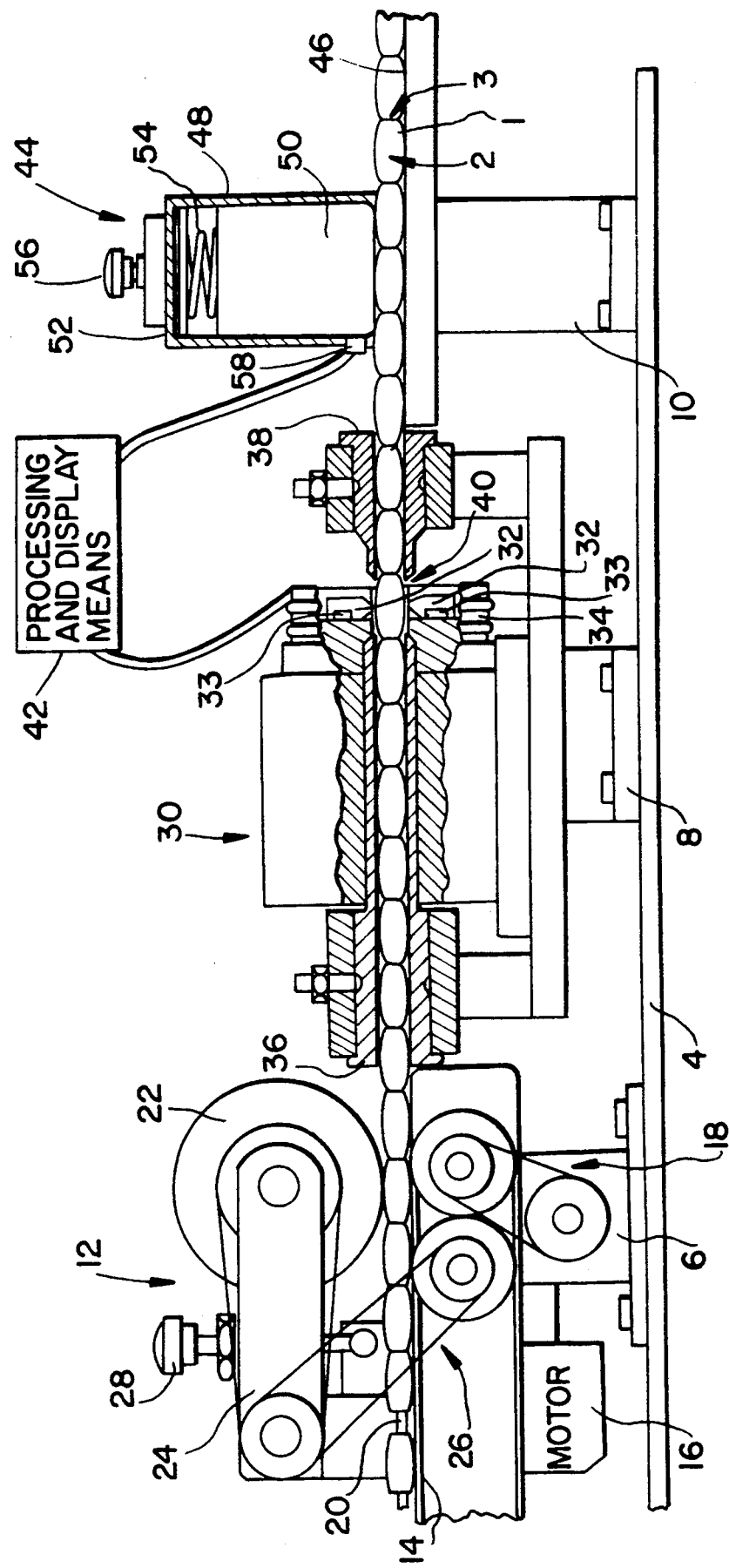

APPARATUS FOR NON-CONTACT DYNAMIC INSPECTIONS OF A PLURALITY OF PIECES

TECHNICAL FIELD

The invention relates to an apparatus for checking features of a plurality of mechanical pieces, with support means for carrying the pieces to be checked, centering means, coupled to the support means, for positioning the pieces in a row, thrust means for urging the pieces along a feed direction and checking means.

BACKGROUND ART

DE-B-1100302 discloses an apparatus for measuring the diameter of workpieces coming out of a centreless grinding machine. The apparatus comprises a first conveying belt moving forward the workpieces, arranged on a guiding device, at a speed higher than that they have through the grinding machine, so that gaps arise between adjacent workpieces, a sliding guide receiving the workpieces from the first conveying belt, a retractable second conveying belt adapted to engage the workpieces under spring pressure for moving them on the sliding guide, a locking device for stopping the workpieces on the sliding guide, and a retractable measuring head for subsequently measuring the workpieces. The measurement of each workpiece is performed while the respective workpiece and other workpieces adjacent to it are stationary.

DE-B-1100302 also refers to a prior art apparatus in which the pieces to be checked are continuously moved, arranged in a row, past a contact type gauge.

It is known from U.S. Pat. No. 3,975,829 to carry out checkings—in particular dimensional checkings—of a plurality of pieces that have been machined by a machine tool. The pieces have a substantially cylindrical shape, and are arranged on a conveyor made of bars, the latter provide aligning and guiding in a determined direction, while a measuring head checks diametral dimensions of the pieces so aligned, during a translation displacement in said direction.

It is also known to carry out "non-destructive" tests of mechanical pieces to inspect the structural integrity after the machining by machine tools. These tests are of fundamental importance in mass production, in order to meet very strict specifications relating to the reliability and the safety of components subject to stresses.

In the specific case of rollers for bearings, it is important to check the presence of flaws or cracks, particularly on the rolling surfaces, that may appear during finishing operations carried out by honing machines like, for example, the one disclosed in German patent application DE-A-3707335.

In order to accomplish these checkings, there can be used "non-contact" probes, like eddy current probes, that scan the surface involved, by performing reciprocally combined translation and rotational displacements between probe and piece. More specifically, these reciprocal displacements can be achieved by causing, respectively, the roller to translate along the direction of its axis and a detection part of the probe to rotate, together with an associated annular support, about said axis.

As the surface defects of the pieces follow a casual statistical distribution, it is not sufficient to perform sample checkings, but it is necessary to inspect all the pieces. To this purpose, at the exit of the honing machine the rollers can be conveyed and guided in a row by a conveyor towards the detection probes, that rotate and scan the rotation surfaces of the pieces.

In the case of "barrel" shaped rollers, the carrying out of checking operations is difficult, due to problems in the positioning of the rollers. In fact, owing to the convex profile of their lateral surfaces, when the pieces are supported on a conveyor on relevant lateral surfaces they are subject to oscillations about transversal axes in consequence of the conveyor displacements, and the piece axes also oscillate and do not stand aligned along the feed direction. It is obvious that similar oscillations prejudice the possibility of detecting surface defects by means of detection probes.

On the other hand, the possible resting of the rollers on plane surfaces, with their associated axes lying in a perpendicular direction with respect to the conveyor feed direction, in a similar way to what is shown in U.S. Pat. No. 3,975,829 (considering pieces of a different type), makes it difficult, and in any case considerably complicated, to perform a check in series of the lateral surfaces of different pieces in the formerly briefly described manner.

U.S. Pat. No. 4,864,239 relates to an apparatus for inspecting cylindrical parts, such as roller bearings, by means of an eddy-current probe. A determined number of parts is loaded onto a cradle device including three rollers and spring loaded end stops that abut the neighboring parts into a stack.

The parts are made to rotate about a longitudinal axis by the rollers of the cradle device, while the eddy-current probe is displaced, step-wise or continuously, along the longitudinal direction.

U.S. Pat. No. 3,863,352 relates to a gauging device for measuring workpieces, such as rings, as they are discharged from a grinding machine.

The workpieces leaving the grinding machine move on guide means having a downward inclination and then enter into contact with a drive endless belt that displaces them at a determined speed toward a gauging station including a gauging device for measuring the thickness of the workpieces.

SUMMARY OF THE INVENTION

Object of the invention is to provide a checking apparatus that allows checkings in series of features of a plurality of mechanical pieces and overcomes the piece positioning problems typically encountered in the known checking methods and apparatuses.

The main result achieved by the apparatus according to the invention is the attainment of an automatic checking of features of pieces, more specifically, a dynamic checking in a non-contact way of the surface features of pieces having rotational symmetry, in the course of which the pieces are automatically positioned and centered in a simple and safe way.

One of the advantages offered by the invention is the possibility of accomplishing an automatic checking in series of the whole rotation surfaces of pieces having a rotational symmetry, be they either of a cylindrical or non-cylindrical shape, in a rapid and reliable way.

BRIEF DESCRIPTION OF THE DRAWING

A preferred embodiment of the invention is now described with reference to the accompanying drawing given by way of non-limiting example, in which the FIGURE shows a schematical side view with some details shown cross-sectioned of an apparatus for checking barrel shaped rollers.

DETAILED DESCRIPTION OF THE INVENTION

The FIGURE illustrates an apparatus for carrying out in series non-destructive checkings of surface features of pieces 1, like barrel shaped rollers having an axis of symmetry, a lateral rotation surface 2, or convex rolling surface, and a pair of opposite surfaces 3, substantially plane and perpendicular to the axis of symmetry. The apparatus can detect the presence of cracks on the rolling surfaces 2 of the pieces.

In said apparatus, support means comprise a bed 4 and support elements 6, 8 and 10 fixed to the bed 4.

A feed station 12, coupled to the bed 4 by means of the support element 6, collects the pieces 1 at the exit of a machine tool—for example a finishing or honing machine, not shown in the FIGURE—whereby they have been machined. In the station 12, support means comprise feed devices with, for example, a conveyor belt 14. Control means comprise a motor 16 and transmission elements 18 with gears, belts and driving pulleys for controlling the displacements of conveyor belt 14. The pieces 1 rest on the conveyor belt 14—that causes a translation displacement—on their "barrel" shaped machined rolling surfaces 2, and are lined up in a substantially rectilinear row along a longitudinal feed direction. Centering means, coupled to the support means, comprise longitudinal guide elements with a pair of parallel longitudinal bars 20, for transversally defining the row and providing the alignment; only one of the bars is visible in the FIGURE. The centering means further comprise compression means with thrust means including a thrust wheel 22, an associated adjustable support 24 and further transmission elements 26 with gears, belts and pulleys coupled to motor 16 for transmitting to wheel 22 a rotation movement. The peripheral surface of wheel 22 is made of compressible material, for example rubber, and its rest position is adjustable in height through a threaded coupling actuated by means of a knob 28. The peripheral surface of wheel 2 urges pieces 1 in correspondence to a first cutting plane transversal to the longitudinal feed direction, and its rotation transmits a thrust to the row in said feed direction. The coupling of motor 16, transmission elements 18 and further transmission elements 26 is such that the displacements of conveyor belt 14 and wheel 22 are mutually synchronous, in order to avoid strains and slidings on pieces 1 that, even when undergoing the thrust of wheel 22, continue to be conveyed by conveyor belt 14.

A checking station 30, coupled to bed 4 by means of support element 8, comprises checking means—schematically shown in the FIGURE—with two probes 32 of the eddy current type, a rotary support 34 carrying probes 32, and adjustment means 33 for adjusting the radial position of probes 32 on support 34. In the checking station 30, longitudinal guide elements comprise oppositely arranged bushings 36 and 38 that support, guide and center the row of pieces 1, arriving from the feed station 12, along the longitudinal direction. The rotary support 34 has a central opening for the passage of the pieces. The probes 32 rotate, integrally with support 34, about the longitudinal axis defined by the feed direction.

A longitudinal separation space, or gap, 40 between the two opposite ends of bushings 36 and 38, is arranged in correspondence to said central opening of the rotary support 34. The gap 40 enables probes 32, during the rotation of support 34, to scan the surface 2 of each roller 1. The distance existing between the adjacent ends of bushings 36 and 38 is in actual fact definitely smaller than that shown—for the sake of simplicity—in the FIGURE. Considering pieces 1 to be checked having a length of about 10 mm., 2 mm. may be a typical value for such distance.

Processing and display means—schematically illustrated in the FIGURE and indicated by reference number 42—are connected to probes 32 in order to receive electric signals, process and display information relevant to surface features of the checked pieces.

An exit station 44, coupled to bed 4 by means of support element 10, comprises a supporting surface 46 whereupon pieces 1, lined up in a row, arrive after the checking operation, and are conveyed towards gathering and sorting units of a known type, not shown in the FIGURE. Compression means at the exit station 44 comprise braking means 48, schematically shown in the FIGURE, consisting of a friction shoe 50, made of plastic material and associated support frame 52 coupled to the support element 10 in a way not shown in the FIGURE. Shoe 50 is coupled to frame 52 in a way that shoe 50 itself is resiliently urged to contact—with an adjustable force directed towards surface 46—pieces 1, in correspondence to a second cutting plane transversal to the feed direction. A spring 54 and a knob 56, schematically show these features in the FIGURE. The force is adjusted in such a way that shoe 50 applies to pieces 1 arriving from checking station 30, a frictional force that tends to slow down the translation displacement of the row along the feed direction, without, however, stopping such a displacement.

The functioning of the apparatus is the following.

Further to the machining by a machine tool, as, for example, a honing machine, pieces 1 are placed on the conveyor belt 14 at the feed station 12 and approximately lined up in a longitudinal row by bars 20. The pieces 1 translate along the feed direction due to the displacement of conveyor belt 14, and reach wheel 22 which applies to them a thrust in the same direction. The synchronism between the translation displacements of belt 14 and the rotation of wheel 22—both movements being controlled by motor 16—guarantees a correct action on the pieces, that are not subject to strains and/or slidings.

The pieces 1, so lined up in a row and urged by wheel 22, pass through the checking station 30 guided by bushings 36 and 38, until they reach exit station 44 where, in correspondence to the braking means 48, undergo the action of shoe 50 consisting in applying to the row a resisting action through frictional force that opposes to the thrust applied by wheel 22. Said frictional force does not prevent the pieces 1 from continuing their translation along the feed direction, overcoming the braking means 48, towards the gathering and sorting units, but it causes a tightening action with a compression force among the pieces 1 of the row in a section comprised between wheel 22 and shoe 50 and dynamically defined by said first and second cutting planes, said section including the pieces that pass through checking station 30.

In a checking position substantially defined by the gap 40 existing between bushings 36 and 38, the rolling surfaces 2 of the pieces 1 are scanned by probes 32, by virtue of the combined rotations of support 34 and the translations of pieces 1. The previously described tightening action of the compression means, that is of the oppositely arranged thrust and braking means, ensures the correct positioning of the barrel rollers 1 at the checking station 30. In fact, the mutual thrust of the surfaces 3 of adjacent rollers 1, that are in contact owing to such a tightening action, prevents undesired displacements of the pieces, as, for example, oscillations on the convex resting surfaces 2, and, in general, displacements causing misalignments between the symmetry axes of rollers I and the longitudinal feed direction.

Further to the aforementioned scanning, probes 32 send electrical signals, responsive to the surface condition of the rolling surfaces 2, to means 42 for the processing and the displaying relevant data and provide said data to appropriate selection units located downstream of the apparatus.

The checking means may comprise additional probes, shown in the FIGURE and identified by reference number 58, connected to the braking means 48 and positioned at a known longitudinal distance from the probes 32. Said distance may be for example a multiple of the length of pieces 1. The additional probes 58 are connected to the processing means 42 and are adapted to emit signals in correspondence to zones of the row where contact occurs between two adjacent rollers 1. As probes 32 generally scan in a continuous way the pieces 1 of the row, in other terms the translation of the row and the rotation of support 34 are continuous, the signals sent by probes 58 are used for monitoring when a zone of contact between two rollers 1 is in the gap 40, that is they indicate the passage from one roller 1 to a following one in the checking position and stop, in correspondence to said passage, the processing by means 42 of the signal sent by probes 32.

Probes 32 are of a known type for performing eddy current checks of the surface condition of pieces 1, and their transversal position on the rotary support 34 during the checking, that is their distance from the rolling surface 2, is adjustably fixed through adjustment means 33. In the case of barrel rollers, said transversal (or radial) position of probes 32 on the support 34 may be dynamically adjusted in the course of the checking operations of each piece 1, in order to keep said distance from surface 2 substantially unchanged, following the variations of the diametral dimensions of the piece 1. To this end, the processing means 42 are connected to adjustment means 33, to control the latter on the base of either the signals from probes 32, or signals from further probes (not shown in the FIGURE), which detect diametral variations of each piece 1 passing through the checking station In the case of barrel rollers having small diametral variations, such adjustments in the radial position of probes 32 may be unnecessary, and a compensation for changes in the distance existing between the probes 32 and the rolling surface 2 may be carried out, for example, through known electronic dynamic compensating systems.

The described apparatus allows a dynamic inspection in series of the pieces 1, and so renders checking operations of special pieces like barrel rollers, faster than ever. In fact, a checking of such kind of pieces carried out in a previously known way implies selecting, positioning, and inspecting a single one at a time of the pieces to be checked, owing to the positioning problems of said particularly shaped pieces.

A typical inspection operation of barrel rollers having a length of about 10 mm., by way of the described apparatus, allows to check from 1 to 4 pieces in one second.

The action applied by shoe 50 on the row of pieces 1 can be featured in a different way from that illustrated. Shoe 50 can be urged towards the pieces 1, for example, by 10 means of a weight, or according to other methods that however guarantee the previously described frictional action.

Moreover, the thrust and the resisting action can be carried out in a different way from that illustrated in the FIGURE, by exploiting, for-example, the weight of the pieces, and/or suitable tiltings of the support means and/or centering means, in order to cause a thrust in the feed direction and the opposed resisting force. All the different ways to obtain the thrust and the resisting action must anyway guarantee the providing of the compression force among the pieces 1 of the row.

According to a different embodiment the row is guided also in the gap 40 existing between bushings 36 and 38, that is in correspondence to the zone where the check is performed. To this purpose there can be foreseen a tube for connecting bushing 36 to bushing 38; said tube is made of non-magnetic material (for example plastic) in order not to affect the correct functioning of probes 32.

According to a further embodiment the centering means can be provided, for example, by a tube of non-magnetic material, and the feed direction need not necessarily be rectilinear.

In an apparatus substantially similar to the one shown there can also be foreseen checking means different from the probes 32, such as, for example, optical heads for checking the surface condition, or heads for accomplishing non-contact dimensional checkings of the pieces, like checkings of diametral dimensions.

I claim:

1. Apparatus for checking features of a plurality of pieces (1) featuring rotational symmetry about a longitudinal geometric axis, comprising support means (4 to 10);

centering means (20, 22, 36, 38), coupled to the support means (4 to 10), for arranging the pieces (1) to be checked in a row, the centering means defining a longitudinal feed direction;

thrust means (14, 22), coupled to the support means (4 to 10), for urging the pieces (1) along said feed direction;

braking means (48) for applying to the pieces (1) a braking action opposing the thrust action applied by the thrust means (14, 22), the thrust action prevailing over the braking action; and checking means (32, 58) of non-contact type arranged, near said centering means (36, 38), in a position longitudinally lying between the thrust means (14, 22), and the braking means (48), whereby pieces (1) having convex lateral surface and plane end surfaces can be checked while continuously passing before the checking means, with the ends of adjacent pieces in stable contact with one another and the geometric axes aligned along the longitudinal feed direction.

2. An apparatus as claimed in claim 1, wherein the thrust means comprise a belt conveyor (14) and a thrust wheel (22) contacting the lateral surface of the pieces (1), the belt conveyor (14) and the thrust wheel (22) being synchronously driven.

3. An apparatus according to claim 1, wherein the braking means include a friction shoe (50) resiliently urged against the lateral surface of the pieces (1).

4. An apparatus according to claim 1, wherein the checking means include a rotary support (34), eddy current probe means (32) carried by the rotary support (34) and processing means (42) for processing the signals of the probe means (32).

5. An apparatus according to claim 4, wherein the checking means comprise adjustment means (33) for adjusting the position of the probe means (32) on the rotary support (24).

6. An apparatus according to claim 4, wherein the checking means include additional probe means (58) for providing to the processing means (42) a signal indicating the passage of zones of contact between adjacent pieces (1).

* * * * *

UNITED STATES PATENT AND TRADEMARK OFFICE
CERTIFICATE OF CORRECTION

PATENT NO. : 5,361,027
DATED : November 1, 1994
INVENTOR(S) : Narcisco SELLERI

It is certified that error appears in the above-indentified patent and that said Letters Patent is hereby corrected as shown below:

Column 2, line 67, the ".(period)" appearing after "apparatus" should be deleted.

Column 5, line 45, "base" should read -- basis --.

line 49, --   .(period) -- should appear after "station".

Column 6, line 4, "10" appearing after "by" should be deleted.

Signed and Sealed this

Seventh Day of February, 1995

Attest:

BRUCE LEHMAN

Attesting Officer      Commissioner of Patents and Trademarks